United States Patent
Vanderpool et al.

(12) 
(10) Patent No.: US 11,241,253 B2
(45) Date of Patent: *Feb. 8, 2022

(54) SUBCUTANEOUS DELIVERY TOOL

(71) Applicant: Medtronic, Inc., Minneapolis, MN (US)

(72) Inventors: Matthew T. Vanderpool, Minneapolis, MN (US); Michael R. Klardie, Bloomington, MN (US); Kris A. Peterson, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/329,986

(22) Filed: May 25, 2021

(65) Prior Publication Data

US 2021/0275221 A1    Sep. 9, 2021

Related U.S. Application Data

(63) Continuation of application No. 14/204,227, filed on Mar. 11, 2014.

(Continued)

(51) Int. Cl.
*A61B 17/3209*    (2006.01)
*A61B 17/32*    (2006.01)
(Continued)

(52) U.S. Cl.
CPC .... *A61B 17/3468* (2013.01); *A61B 17/32093* (2013.01); *A61B 5/283* (2021.01);
(Continued)

(58) Field of Classification Search
CPC .......... A61B 17/3468; A61B 17/32093; A61B 5/283; A61B 2017/320044;
(Continued)

(56) References Cited

U.S. PATENT DOCUMENTS

| 2,009,393 | A | 7/1935 | Gioacchino |
|---|---|---|---|
| 4,915,686 | A | 4/1990 | Frederick |

(Continued)

FOREIGN PATENT DOCUMENTS

| CN | 1031481 A | 3/1989 |
|---|---|---|
| CN | 2621634 Y | 6/2004 |

(Continued)

OTHER PUBLICATIONS

First Office Action and Search Report, and translation thereof, from counterpart Chinese Application No. 201480015082.5, dated Mar. 20, 2017, 18 pp.

(Continued)

*Primary Examiner* — Jing Rui Ou
(74) *Attorney, Agent, or Firm* — Shumaker & Sieffert, P.A.

(57) ABSTRACT

Subcutaneous implantation tools and methods of implanting a subcutaneous device using the same. The tool may include a tool body having a longitudinally extending recess having a distal opening and having a tunneler at a distal end of the tool body extending from the distal opening of the recess. The tool may include a plunger slidably fitting within at least a portion of the tool body recess. The recess may be configured to receive an implantable device and the tunneler preferably extends distally from the recess at a position laterally displaced from the device when the device is so located in the recess. Movement of the plunger distally within the recess advances the device distally out of the recess and alongside of and exterior to the tunneler.

30 Claims, 9 Drawing Sheets

Related U.S. Application Data

(60) Provisional application No. 61/788,940, filed on Mar. 15, 2013.

(51) Int. Cl.

| | |
|---|---|
| *A61B 17/34* | (2006.01) |
| *A61N 1/375* | (2006.01) |
| *A61N 1/372* | (2006.01) |
| *A61B 5/283* | (2021.01) |

(52) U.S. Cl.
CPC ............ *A61B 2017/320044* (2013.01); *A61B 2017/320056* (2013.01); *A61N 1/3756* (2013.01); *A61N 1/37205* (2013.01)

(58) Field of Classification Search
CPC .... A61B 2017/320056; A61N 1/37205; A61N 1/3756
See application file for complete search history.

(56) References Cited

U.S. PATENT DOCUMENTS

| | | | |
|---|---|---|---|
| 5,127,404 A | 7/1992 | Wyborny et al. | |
| 5,304,119 A | 4/1994 | Balaban et al. | |
| 5,484,403 A | 1/1996 | Yoakum et al. | |
| 5,562,613 A * | 10/1996 | Kaldany | A61B 10/0275 |
| | | | 600/567 |
| 5,842,999 A | 1/1998 | Pruitt | |
| 5,772,671 A | 6/1998 | Harmon | |
| 5,954,670 A | 9/1999 | Baker | |
| 5,987,352 A | 11/1999 | Klein et al. | |
| 6,230,059 B1 | 5/2001 | Duffin | |
| 6,412,490 B1 | 7/2002 | Lee | |
| 7,035,684 B2 | 4/2006 | Lee | |
| 8,888,745 B2 | 11/2014 | Van Der Graaf et al. | |
| 10,786,279 B2 | 9/2020 | Vanderpool et al. | |
| 2001/0029386 A1 * | 10/2001 | Matsutani | A61F 9/0133 |
| | | | 606/166 |
| 2004/0082969 A1 | 4/2004 | Kerr | |
| 2004/0193154 A1 | 9/2004 | Leatherbury et al. | |
| 2004/0249388 A1 | 12/2004 | Michelson | |
| 2005/0090852 A1 | 4/2005 | Layne et al. | |
| 2005/0096645 A1 | 5/2005 | Wellman et al. | |
| 2005/0107768 A1 | 5/2005 | Ting | |
| 2006/0074434 A1 | 4/2006 | Wenstrom, Jr. et al. | |
| 2006/0097331 A1 | 5/2006 | Hattori et al. | |
| 2006/0106415 A1 | 5/2006 | Gabbay | |
| 2006/0174898 A1 | 8/2006 | Brown | |
| 2007/0010738 A1 | 1/2007 | Mark et al. | |
| 2007/0179515 A1 | 8/2007 | Matsutani et al. | |
| 2007/0249992 A1 | 10/2007 | Bardy | |
| 2008/0154298 A1 | 6/2008 | Grayzel et al. | |
| 2009/0030426 A1 | 1/2009 | Zinn et al. | |
| 2009/0036917 A1 | 2/2009 | Anderson | |
| 2009/0137946 A1 | 5/2009 | Nassiri et al. | |
| 2010/0030227 A1 | 2/2010 | Kast et al. | |
| 2010/0094252 A1 | 4/2010 | Wengreen et al. | |
| 2010/0198140 A1 | 8/2010 | Lawson | |
| 2010/0324578 A1 * | 12/2010 | Bardy | A61M 37/0069 |
| | | | 606/167 |
| 2010/0331868 A1 | 12/2010 | Bardy | |
| 2012/0283705 A1 | 11/2012 | Lee et al. | |
| 2014/0128963 A1 | 5/2014 | Quill et al. | |
| 2014/0276928 A1 | 9/2014 | Vanderpool et al. | |
| 2016/0175007 A1 | 6/2016 | Valbuena et al. | |
| 2017/0258346 A1 | 9/2017 | Vanderpool et al. | |
| 2020/0129206 A1 | 4/2020 | Cornelius et al. | |
| 2020/0383702 A1 | 12/2020 | Vanderpool et al. | |
| 2021/0153895 A1 | 5/2021 | Vanderpool et al. | |

FOREIGN PATENT DOCUMENTS

| | | |
|---|---|---|
| CN | 2702718 Y | 6/2005 |
| CN | 202342097 U | 7/2012 |
| DE | 469951 C | 1/1929 |
| DE | 4243641 A1 | 9/1994 |
| EP | 3034128 A1 | 6/2016 |
| JP | 2001502937 A | 3/2001 |
| JP | 2007516031 A | 6/2007 |
| JP | 2008528084 A | 7/2008 |
| JP | 2011092065 A | 5/2011 |
| WO | 9813091 A1 | 4/1998 |
| WO | 2005044116 A2 | 5/2005 |
| WO | 2005060306 A1 | 6/2005 |
| WO | 2008016551 A1 | 2/2008 |
| WO | 2012098356 A1 | 7/2012 |

OTHER PUBLICATIONS

Notice on the Second Office Action, and translation thereof, from counterpart CN Application No. 201480015082.5, dated Mar. 5, 2018, 9 pp.
Third Office Action, and translation thereof, from counterpart Chinese Application No. 201480015082.5, dated Apr. 7, 2020, 13 pp.
Decision on Reexamination from counterpart Chinese Application No. 201480015082.5, dated Sep. 11, 2019, 11 pp.
The Decision on Rejection, and translation thereof, from counterpart Chinese Application No. 201480015082.5, dated Dec. 5, 2019, 14 pp.
Fourth Office Action, and translation thereof, from counterpart Chinese Application No. 201480015082.5, dated Jun. 22, 2020, 13 pp.
The Notification of Rejection, and translation thereof, from counterpart Chinese Application No. 2014-80015082.5, dated Nov. 4, 2020, 11 pp.
Preliminary Amendments filed in counterpart European Patent Application No. 14717919.6, filed on Oct. 9, 2015, 9 pp.
Communication Pursuant to Rules 161(1) and 162 EPC from counterpart European Application No. 14717919.6, dated Nov. 4, 2015, 2 pp.
Response to Communication Pursuant to Rules 161(1) and 162 EPC, dated Nov. 4, 2015, from counterpart European Application No. 14717919.6, filed May 13, 2016 5 pp.
Communication pursuant to Article 94(3) EPC (examination report) from counterpart European Patent Application No. 14717919.6 dated Jul. 28, 2017, 5 pp.
Response to the Communication pursuant to Article 94(3) EPC (examination report), dated Jul. 28, 2017, from counterpart European Patent Application No. 14717919.6, filed Dec. 6, 2017, 13 pp.
Intent to Grant from counterpart European Application No. 14717919.6, dated Apr. 16, 2018, 30 pp.
Decision to Grant from counterpart European Application No. 14717919.6, dated Jun. 9, 2018, 1 pp.
Extended European Search Report from counterpart European Patent Application No. 18188908.0, dated Oct. 19, 2018, 7 pp.
Response to Communication Pursuant to Rule 69 EPC dated Jan. 7, 2019 and the Extended European Search Report dated Oct. 19, 2018, from counterpart European Application No. 18188908.0, filed Apr. 15, 2019, 13 pp.
Office Action, and translation thereof, from counterpart Japanese Patent Application No. 2016-501382, dated Oct. 29, 2017, 7 pp.
Decision to Grant and translation thereof, from counterpart Japanese Application No. 2016-501382, dated Jun. 26, 2018, 5 pp.
Notice of Reasons for Refusal and translation thereof, from counterpart Japanese Application No. 2018-137778, dated Jun. 25, 2019, 15 pp.
Notice of Reasons for Refusal, and translation thereof, from counterpart Japanese Application No. 2018-137778, dated Jun. 28, 2019, 12 pp.
Office Action, and translation thereof, from counterpart Japanese Application No. 2018137778, dated Feb. 6, 2020, 3 pp.
International Search Report and the Written Opinion from International Application No. PCT/US2014/023912, dated Jun. 20, 2014, 9 pp.
International Preliminary Report on Patentability from International Application No. PCT/US2014/023912, dated Sep. 15, 2015, 5 pp.

(56) References Cited

OTHER PUBLICATIONS

Prosecution History from U.S. Appl. No. 14/204,227, dated Nov. 5, 2015 through May 10, 2021, 461 pp.
Prosecution History from U.S. Appl. No. 15/610,076, dated Aug. 7, 2017 through Aug. 3, 2020, 198 pp.
U.S. Appl. No. 17/165,304, filed Feb. 2, 2021, naming inventors Vanderpool et al.
U.S. Appl. No. 17/323,298, filed May 18, 2021, naming inventors Vanderpool et al.
U.S. Appl. No. 29/748,593, filed Aug. 31, 2020, naming inventors Vanderpool et al.
U.S. Appl. No. 29/748,588, filed Aug. 31, 2020, naming inventors Vanderpool et al.
U.S. Appl. No. 17/325,873, filed May 20, 2021, naming inventors Vanderpool et al.
U.S. Appl. No. 17/325,904, filed May 20, 2021, naming inventors Vanderpool et al.
Examination Report from counterpart European Application No. 18188908.0, dated May 26, 2021, 7 pp.
U.S. Appl. No. 29/803,137, filed Aug. 10, 2021, naming inventors Vanderpool et al.
U.S. Appl. No. 29/803,142, filed Aug. 10, 2021, naming inventors Vanderpool et al.
Prosecution History from U.S. Appl. No. 14/204,227, dated Nov. 5, 2015 through Sep. 8, 2021, 486 pp.
Prosecution History from U.S. Appl. No. 17/323,298, dated Sep. 9, 2021, 16 pp.
Prosecution History from U.S. Appl. No. 17/325,873, dated Sep. 3, 2021, 14 pp.
Prosecution History from U.S. Appl. No. 17/325,904, dated Aug. 11, 2021 through Aug. 18, 2021, 25 pp.
Response to Examination Report from counterpart European Application No. 18188908.0, dated May 26, 2021, filed Sep. 30, 2021, 24 pp.
Notice of Allowance from U.S. Appl. No. 14/204,227 dated Nov. 3, 2021, 10 pp.

* cited by examiner

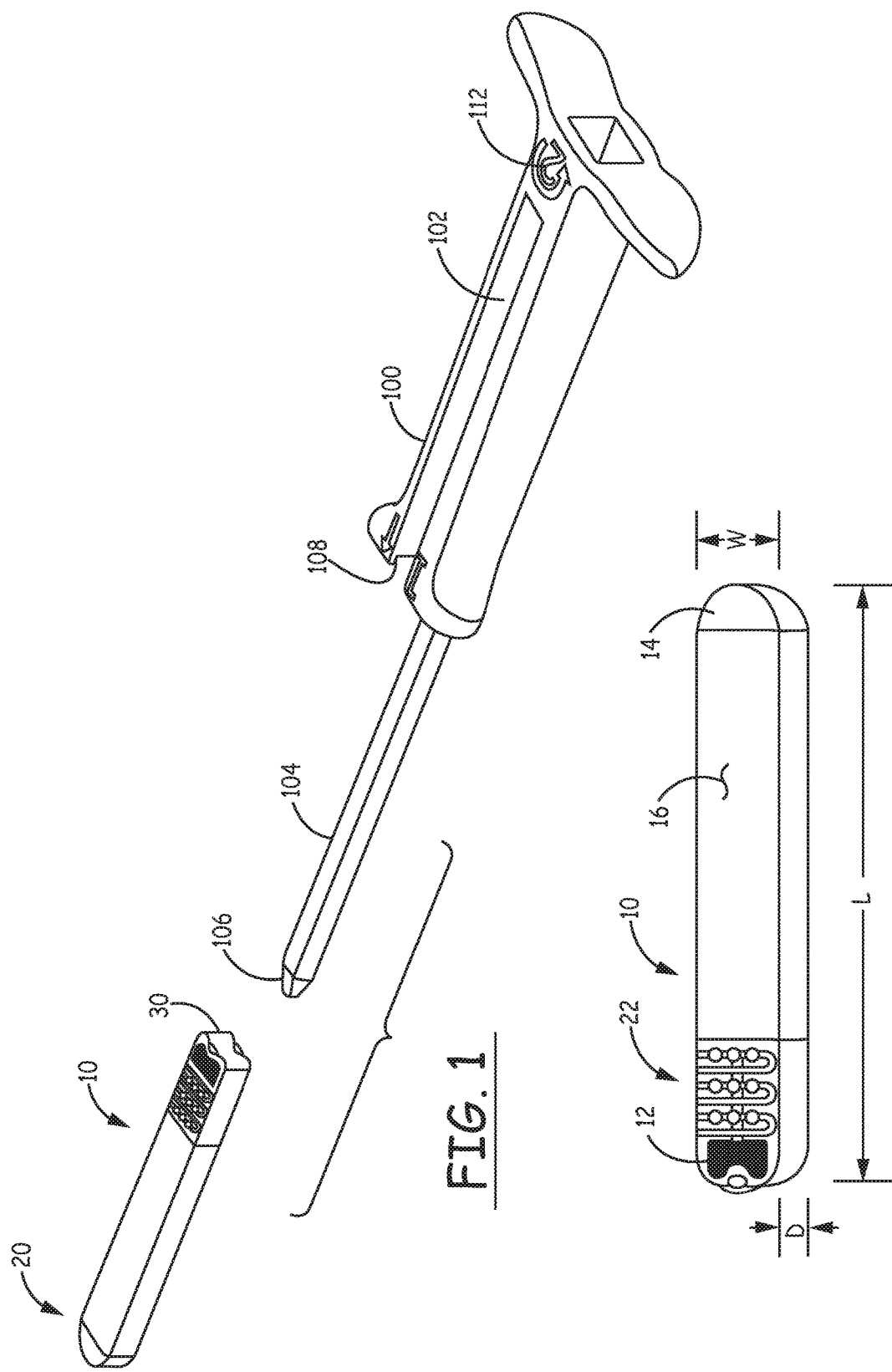

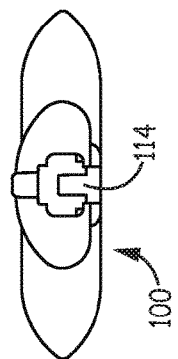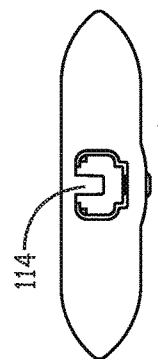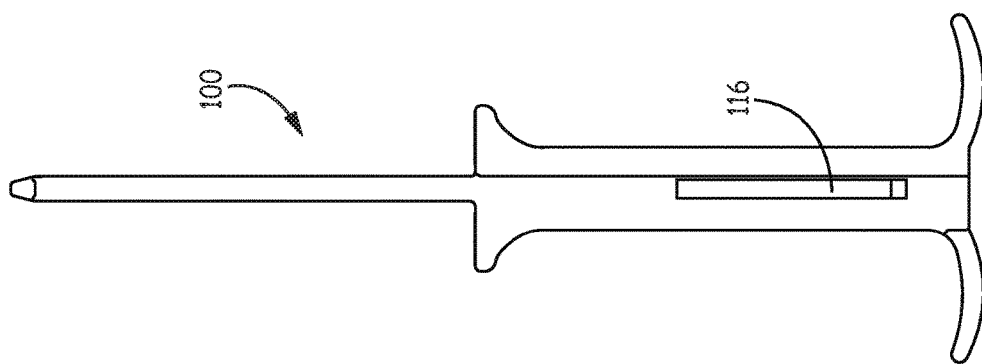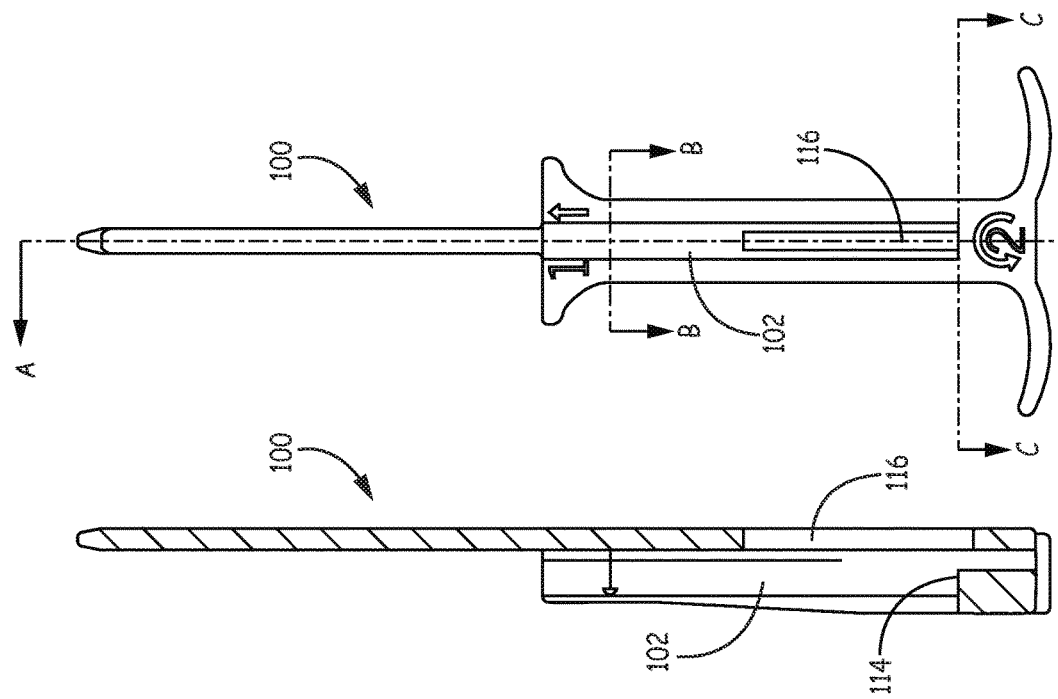

SUBCUTANEOUS DELIVERY TOOL

This application is a continuation of U.S. patent application Ser. No. 14/204,227, filed Mar. 11, 2014, which claims the benefit of U.S. Provisional Application No. 61/788,940, filed Mar. 15, 2013. The entire content of each of these applications is incorporated herein by reference.

BACKGROUND

The use of monitoring equipment to measure various physical parameters of a patient is well known. There is a growing demand for using subcutaneous monitoring devices, which allow doctors to obtain information without a patient being connected to an external machine and/or which may otherwise not be reproducible in office settings. The term subcutaneous generally implies locations within the body of a patient under the skin and exterior to the musculature beneath the skin. For example, an implantable device that includes the ability to monitor a patient's heart beat in order to detect transient symptoms suggesting cardiac arrhythmia allows doctors to review data over a longer period of time than using external monitoring equipment in a simulated testing situation. However, to successfully implant implantable subcutaneous devices an implantation tool should, for example, ensure that the device is not implanted in muscle, reduce contact between the surgeon and the wound, be used in an office setting to minimize patient discomfort and the need for invasive surgery and have the ability to repeatedly recreate the same size incision site in the patient.

Exemplary prior art insertion tools include those illustrated in US Patent Application Publication No. 2010/0094252 by Wengreen, et al., incorporated herein by reference in its entirety.

SUMMARY

Further areas of applicability will become apparent from the description provided herein. It should be understood that the description and specific examples are intended for purposes of illustration only and are not intended to limit the scope of the present disclosure.

Exemplary embodiments provide subcutaneous implantation tools and methods of implanting a subcutaneous micro-device using the same. The invention provides a syringe-like tool, comprising a tool body, hereafter "handle", having a hollow, distally longitudinally extending recess such as a bore or channel and having a distal opening through which the device may be delivered. The device preferably also includes a movable plunger located within the bore or channel. An incision tool is provided to make an incision through which the subcutaneous device is implanted.

The device may, for example, be implanted in the region of the thorax. A specific recommended location will typically be provided within an associated product manual. In one embodiment, two electrodes on the body of the device monitor the patient's subcutaneous ECG. The device may ECG recordings in response to patient activation or in response to automatically detected arrhythmias. Exemplary devices are disclosed in US Patent Application Publication No. 2009/0036917 by Anderson, US Patent Application Publication No. 2010/0094252 by Wengreen, et al., US Patent Application Publication No. 2012/0283705 by Hoeppner, et al., U.S. Pat. No. 5,987,352, issued to Klein, et al., U.S. Pat. Nos. 6,412,490 and 7,035,684 issued to Lee, et al. and U.S. Pat. No. 6,230,059, issued to Duffin, et al., all incorporated herein by reference in their entireties.

The incision tool is designed to create an incision of repeatable width and depth with a single motion. It is composed of a blade, designed to make a repeatable incision, and handle, designed to ergonomically fit the hand. The incision tool is intended to make the incision simple and repeatable. Other mechanisms for making openings in the patient's skin such as trocars, spreaders, scalpels and the like may be substituted in some alternative embodiments. The insertion tool delivers the device through the incision and into the subcutaneous tissue. The tool is designed to ensure the device is delivered into a tight pocket to maximize electrode contact with the surrounding tissue in a highly repeatable manner, and is composed of two parts: a handle and a plunger. The handle is composed of a bore or channel section, used to hold the device and guide it during implant, and a protrusion extending distally of the channel, used to bluntly dissect an implant path for the device to travel down while being implanted. The tunneler extends distally from the channel a position laterally displaced from the device when the device is located in the channel. The plunger is used to push the device distally out of the handle, through the incision, alongside and exterior to the tunneler and along the implant path created by the tunneler to the final implant location.

The device is typically loaded into the channel section of the insertion tool handle and sterile packaged along with both the insertion tool plunger and the incision tool.

The device is locatable within the channel distal to the plunger, so that when the plunger is moved distally, the device advances distally out of the tool body and into the tissue. Typically, the device will take the form of an elongated body, having a length greater than its thickness and width, as illustrated in the published Application No. 2010/0094252, cited above. The device may extend along its longitudinal axis between proximal and distal ends. The longitudinal channel or bore of the tool body may conform at least in part to the outer configuration of the device and more typically to a cross section of the device taken along its longitudinal axis. If the device, like the above discussed device, has a width greater than its depth and/or is otherwise radially asymmetric around its longitudinal axis, this feature allows the device to be advanced into the tissue while maintaining a desired orientation, as discussed in more detail below.

Optimally, the final insertion site of the device is located a short distance from the incision site. As noted above, the handle is preferably provided with an elongated protrusion or tunneler extending distally from the distal opening of the bore, which is insertable into the tissue through the incision to create a path in the tissue, along which the device may be advanced when pushed by the plunger. The distal end of the tunneler when so inserted is preferably located at the desired location of the distal end of the device. The length of the tunneler is thus preferably at least equal to and preferably somewhat greater than the length of the subcutaneous device.

Additional embodiments provide methods of implanting a subcutaneous micro-device, including inserting the dissection body of the tool described by the embodiments of the tool into an implantation site, where the dissection body includes a micro-device, and delivering the micro-device.

BRIEF DESCRIPTION OF DRAWINGS

Exemplary embodiments will be more clearly understood from the following detailed description taken in conjunction with the accompanying drawings. FIGS. 1-10 represent non-limiting, example embodiments as described herein.

FIG. 1 is a perspective view of an exemplary implantable device and the associated tool handle.

FIG. 2 is a perspective view of the exemplary implantable device.

FIG. 3 is a perspective view of the incision tool according to exemplary embodiments.

FIGS. 6A, 6B, 6C, 6D and 6E are distal end, cut-away, top, bottom and proximal end views, respectively, of the tool handle.

FIG. 10 is a flow chart illustrating a method of delivering a device to a subcutaneous site according to exemplary embodiments.

DETAILED DESCRIPTION

Figure 3:
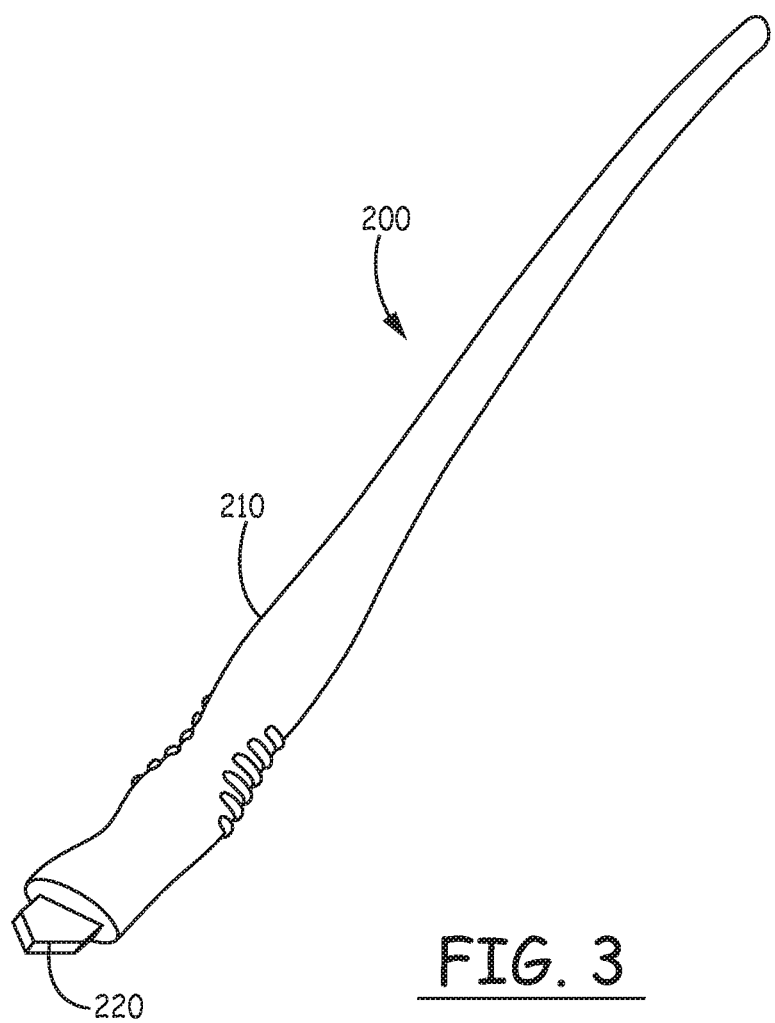

Various exemplary embodiments will now be described more fully with reference to the accompanying drawings in which some exemplary embodiments are illustrated. In the drawings, the thicknesses of layers and regions may be exaggerated for clarity.

Accordingly, while exemplary embodiments are capable of various modifications and alternative forms, embodiments thereof are shown by way of example in the drawings and will herein be described in detail. It should be understood, however, that there is no intent to limit exemplary embodiments to the particular forms disclosed, but on the contrary, exemplary embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of exemplary embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing only particular embodiments and is not intended to be limiting of exemplary embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, e.g., "beneath," "below," "lower," "above," "upper" and the like, may be used herein for ease of description to describe one element or a relationship between a feature and another element or feature as illustrated in the figures. It will be understood that the spatially relative terms are intended to encompass different orientations of the device in use or operation in addition to the orientation depicted in the Figures. For example, if the device in the figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which exemplary embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Exemplary embodiments are directed to subcutaneous implantation tools and methods of implanting subcutaneous micro-devices. FIGS. 1A to 10 illustrate various exemplary embodiments of such subcutaneous implantation tools.

FIG. 1 shows the implantable device 10, aligned longitudinally with the handle 100, arranged for the insertion of device 10 into the channel 102 of the handle 100. The proximal end 20 of the device is inserted into the distal end 108 of the channel 102 of the handle and is advanced proximally until the proximal end 30 of the device is located adjacent an internal stop surface (not illustrated) within the handle 100. At this point, the distal end 20 of the device will be adjacent the distal end 108 of the handle 100. The open upper portion of the channel 102 allows visual verification that the device 10 is properly inserted into the channel. The tunneler 104 extends distally of the distal end 108 of channel 102. The distal end 106 of the tunneler is placed into the incision made by the incision tool with its upper surface facing outward of the patient's body and advanced to provide blunt dissection of the subcutaneous tissue to a point where the distal end 20 of the device is adjacent the opening of the incision. The handle 100 is then rotated 180 degrees so that the tunneler 104 is then above the device (outward relative to the patient's skin). This allows upward pressure on the handle to assist in temporarily enlarging the incision and assures that the device will not escape as advanced distally into the tissue. The device 10 is then advanced by distal movement of the plunger illustrated in FIG. 5B within the channel 102 and along the tunneler 104 until it is properly located within the tissue, displaced distally a short distance from the opening of the incision. The logo 112 assists in reminding the physician to rotate the handle prior to insertion of the plunger and advancement of the device.

FIG. 2 shows the device 10 in more detail. In this view it can be seen that the device comprises two electrodes 12 and 14, located adjacent the proximal and distal ends, respectively, of the device. When implanted, electrode 12, located on the upper surface 16 of the device preferably faces outward toward the skin. As such, when the device is placed into the handle as discussed above, the electrode 12 faces downward and is not visible through the open upper portion of the channel, allowing verification of proper insertion into the handle.

The exemplary device 10 as illustrated generally takes the form of an elongated rectangular prism having rounded corners and a rounded distal end portion. The rounded distal end of the device assists in allowing it to advance into body tissue, providing blunt dissection of the tissue as it advances. Because the cross section of the device is substantially greater than the cross section of the tunneler, the device will be located snugly within the tissue, reducing the chances for the formation of air bubbles adjacent the electrodes and also assisting in maintaining the device in its desired position. The device has length (L), width (W) and depth (D) as illustrated. In this particular embodiment, the with is greater than the depth, providing radial asymmetry along the longitudinal axis of the device and assisting in maintaining the device in its proper orientation with upper surface 16 facing outward after implant. A suture hole 18 may optionally be provided at the proximal end of the device to allow the physician to suture it to underlying tissue if desired. Projections 22 may optionally be provided to prevent longitudinal movement of the device after implant.

As discussed above, the inner surface of the channel of the handle is preferably configured to correspond to the outer configuration of the device. As discussed below in more detail, the configuration of the channel of the handle is configured to engage the rounded corners of the device, preventing rotation of the device within the handle.

FIG. 3 illustrates the incision tool 200, which is provided with a curved plastic handle 210 fitted with a flat, pointed blade 220 having a width equal to the desired width of the incision. The handle is designed to be comfortably held in a position allowing the blade to be advanced through the skin at a shallow angle, avoiding damage to underlying muscle tissue.

Figure 4A:
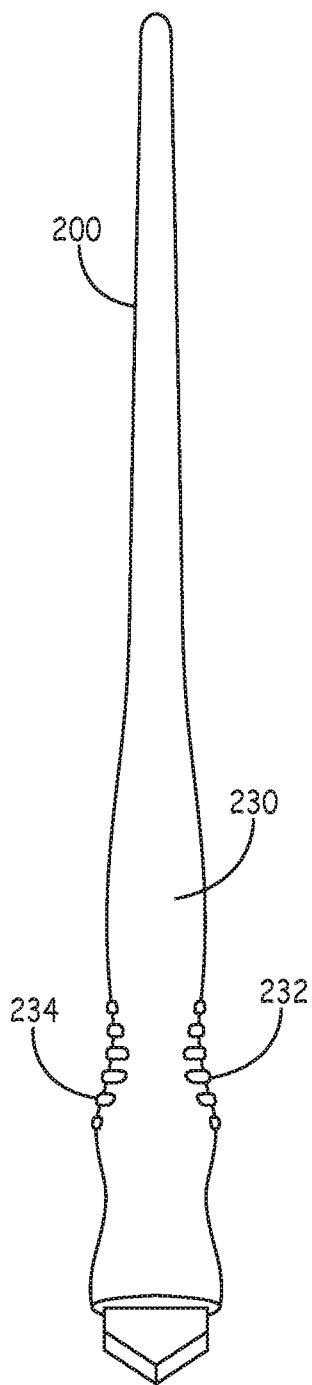
FIGS. 4A, 4B and 4C are top, side and bottom views, respectively, of the incision tool of FIG. 3.
Figure 4B:
Figure 4C:
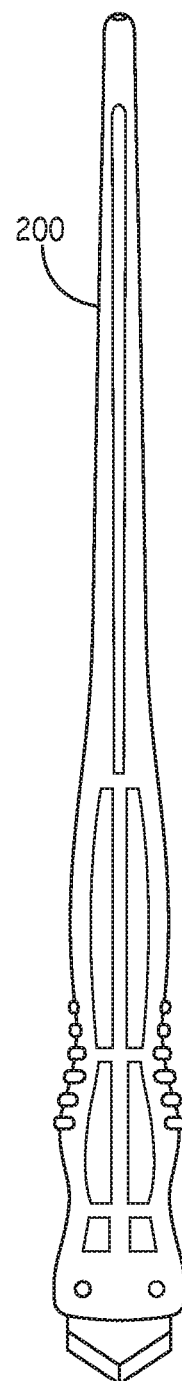

FIGS. 4A, 4B and 4C show top, side and bottom views of the incision device 200. As illustrated in 4A, both the differing coloration of the finger grips 234 and 232 and the placement of the logo 236 on the upper surface assist the physician in assuring that the orientation of the blade is correct to provide the desired shallow penetration angle.

Figure 5A:
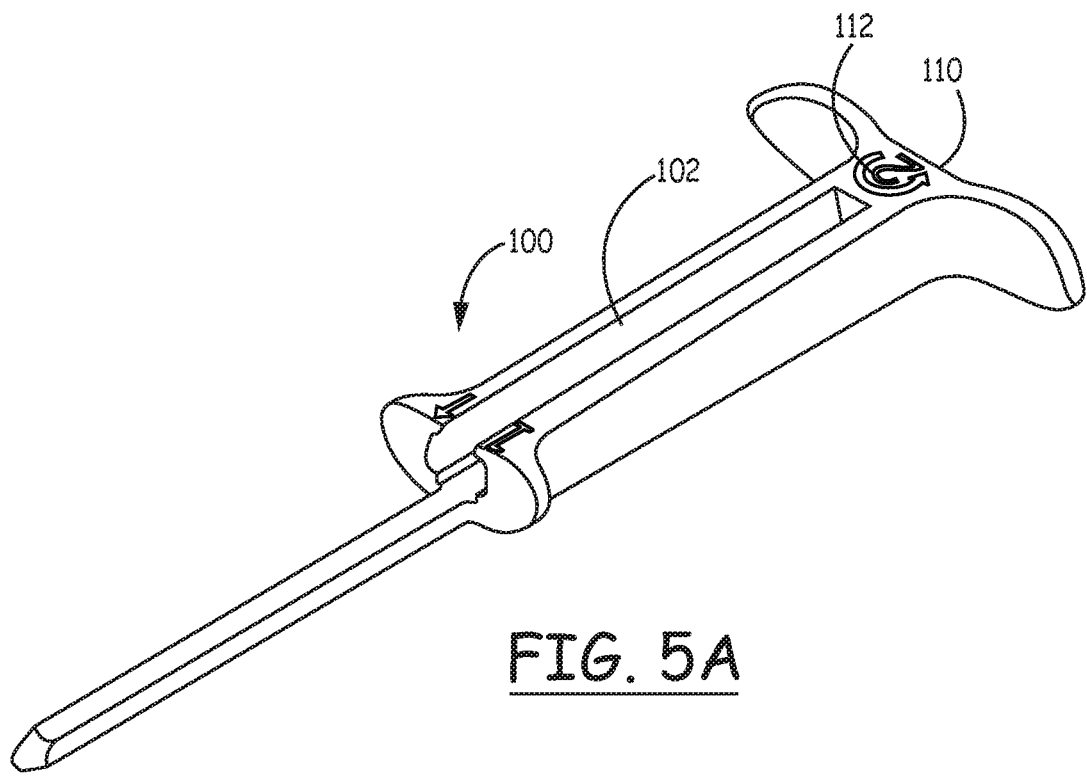
FIGS. 5A and 5B are perspective views of the tool handle and plunger, respectively, according to exemplary embodiments of the invention.
Figure 5B:
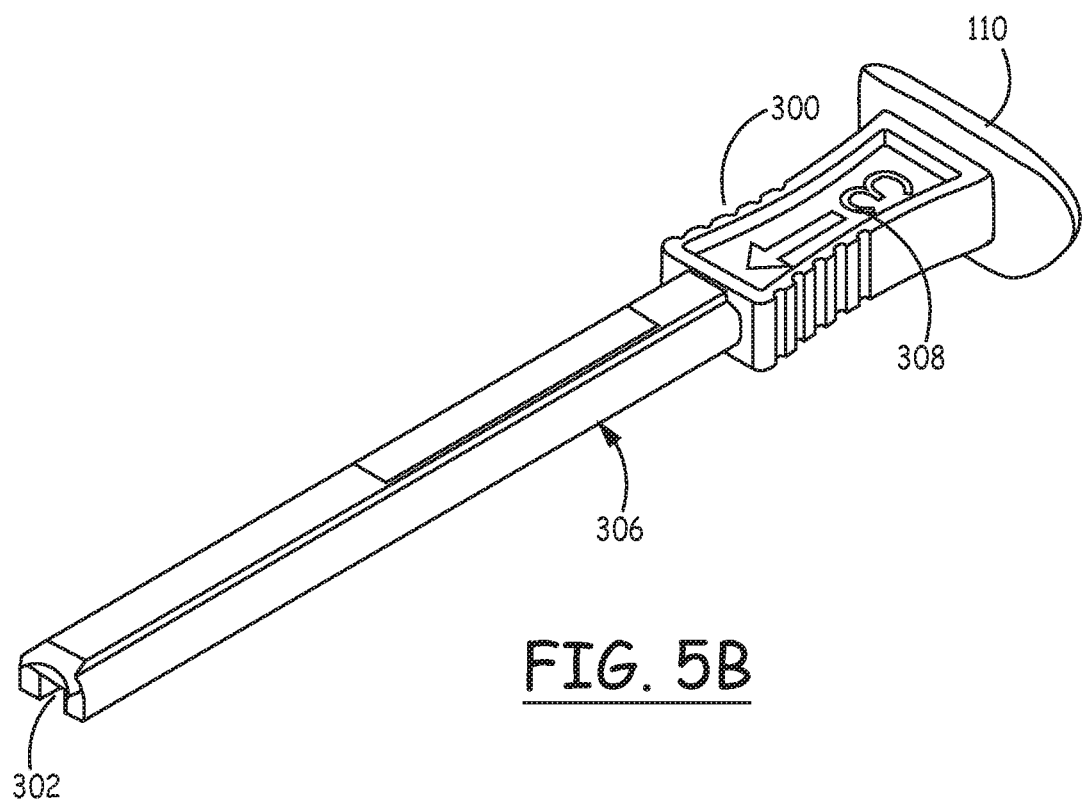

FIGS. 5A and 5B show the handle 100 and the plunger 300 prior to insertion of the plunger into the handle. After rotation of the handle so that its upper surface bearing marking 112 now faces inward toward the patient's skin, the distal end 302 of plunger 300 is then inserted into an opening in the proximal end 110 of the handle and into the channel 102 of the handle.

The plunger is provided with a groove 306 running the length of the lower surface of the plunger up to a distal stop surface discussed below. The opening in the proximal end of the handle includes a protrusion corresponding to the groove in the lower surface of the plunger, assuring its proper orientation within the handle. A marking 308 adjacent the proximal end of the plunger assists the physician in determining that the plunger is in the proper orientation for insertion into the handle.

The plunger is advanced distally, pushing the device into the incision along the then inward facing surface of the tunneler. The device thus follows the path defined by the tunneler to assure proper placement within the tissue. After insertion of the device, the handle and plunger are removed.

Various medical grade materials may be used to form the various parts of the subcutaneous implantation tool, for example, plastics, metals, rubber, sanitizable materials, etc. Exemplary embodiments of the subcutaneous implantation tool may be inexpensive, disposable, etc. The subcutaneous implantation tool may also be configured to be used with known automated injection systems, which use, e.g., compressed air or other inert gases in place of a manual plunger.

FIGS. 6A, 6B, 6C, 6D and 6E are distal end, cut-away, top, bottom and proximal end views, respectively, of the tool handle 100. In these views the projection 114 is visible. Projection 114 provides a distal facing stop surface limiting the insertion of the device 10 into the channel 102. It further engages the slot in the lower surface of the plunger 300, assuring proper orientation of the plunger within the handle. It also provides a proximal facing stop surface limiting distal movement of the plunger. The handle is also show as optionally provided with a slot 116 in its lower surface, through which advancement of the plunger and device can be observed.

Figure 7A:
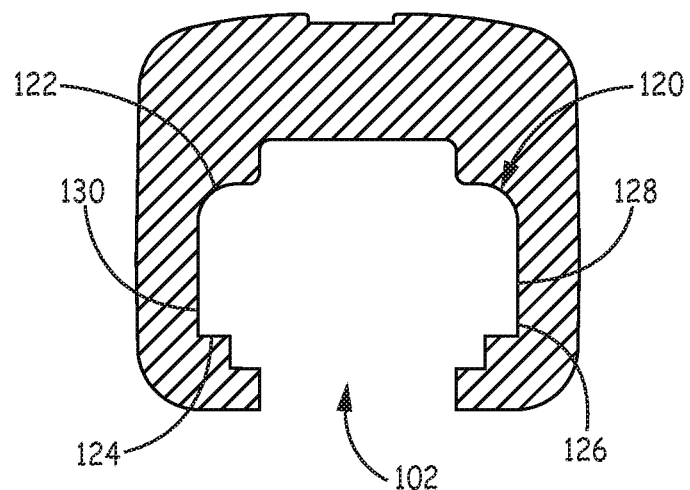
FIGS. 7A and 7B are cross sectional views through the tool handle as illustrated in FIG. 6C.
Figure 7B:
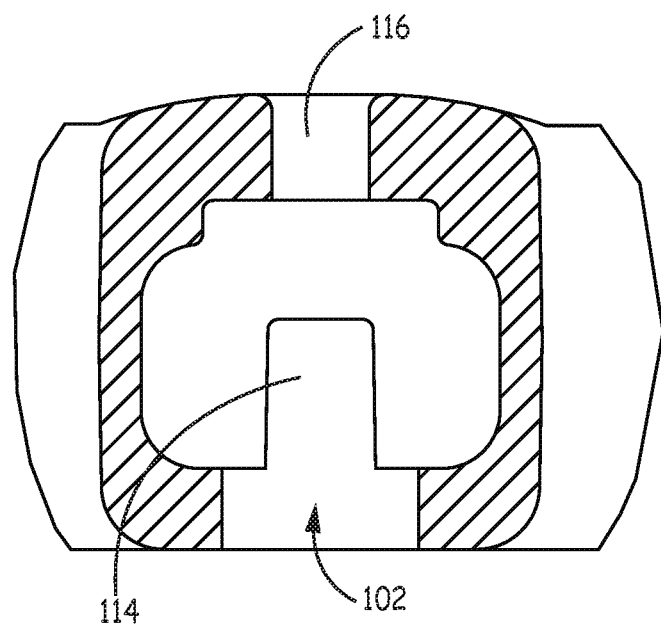

FIGS. 7A and 7B are cross sectional views through the tool handle as illustrated in FIG. 6C. In these views, the arrangement of the inner corner surfaces 12, 122, 124 and 126 can be seen. These surfaces, along with side surfaces 128 and 130, are arranged to generally correspond to the corners and the side surfaces of the device, preventing rotation of the device within the handle. The distal facing surface of projection 114 is also visible in this view.

FIGS. 8A, 8B, 8C and 8D are distal end, cut-away, top and proximal end views, respectively, of the plunger of 5B. In these figures, the configuration of the groove 306 can be seen, along with distally facing stop surface 310, which engages with the proximal facing surface of protrusion 114 of the handle, to limit distal movement of the plunger.

Figure 8B:
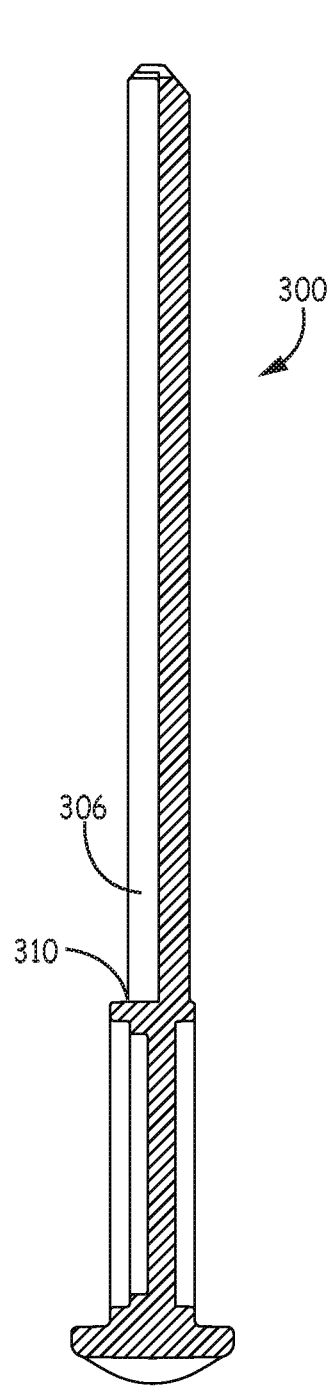
FIGS. 8A, 8B, 8C and 8D are distal end, cut-away, top and proximal end views, respectively, of the plunger of 5B.
Figure 8C:
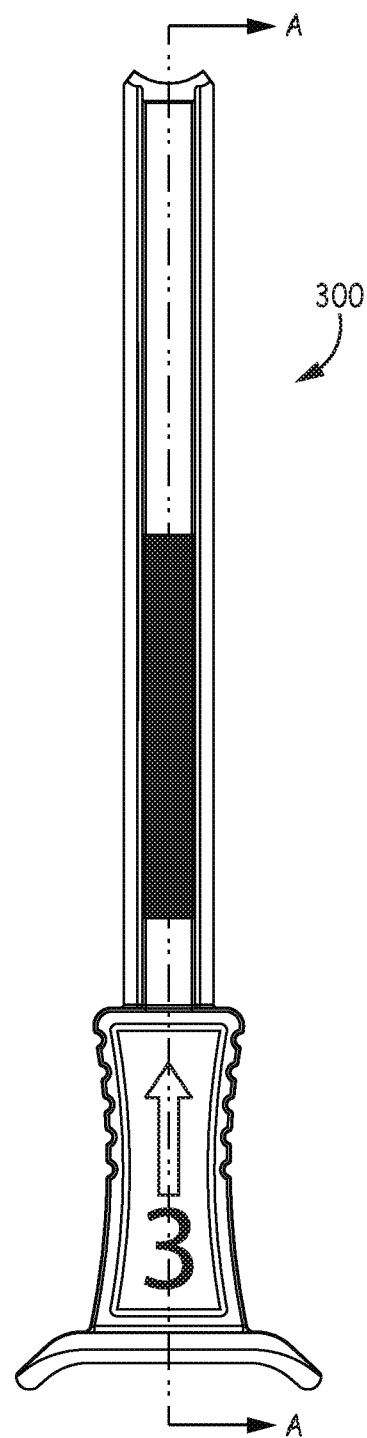
Figure 8A:
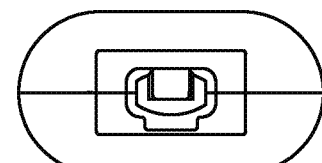
Figure 8D:
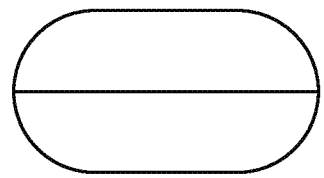
Figure 9B:
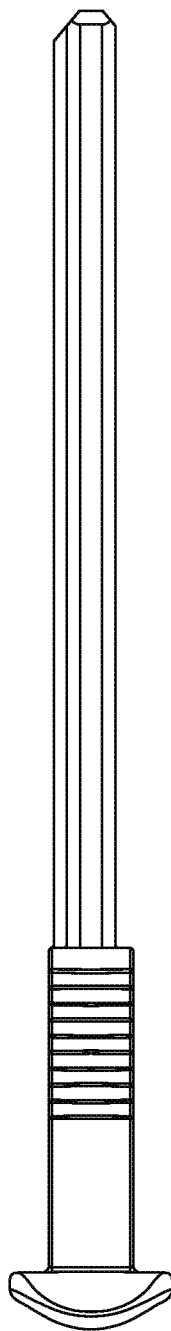
FIGS. 9A, 9B, and 9C are cross sectional, side and bottom views, respectively, of the plunger as illustrated in FIG. 8D.
Figure 9C:
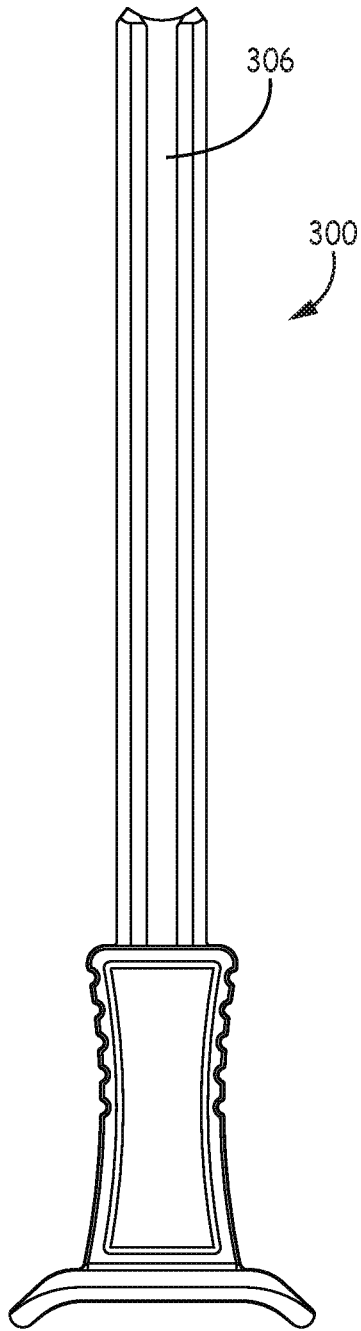
Figure 9A:
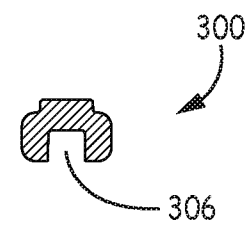

FIGS. 9A, 9B, and 9C are cross sectional, side and bottom views. Respectively, of the plunger as illustrated in FIG. 8D. In these views, the configuration of the groove 306 is visible in more detail.

Figure 10:
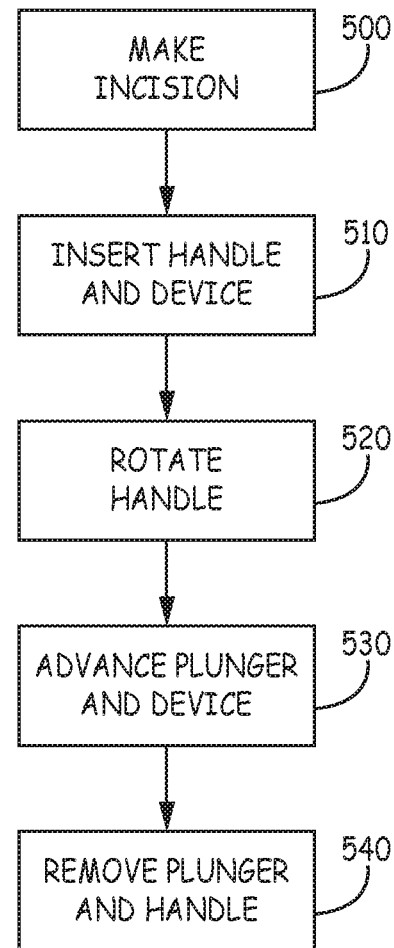

FIG. 10 is a flow chart illustrating a preferred embodiment of an insertion process according to the present invention. At 500, the incision is made using the incision tool. At 510, the handle carrying the device is inserted into the tissue such that the tunneler produces an elongated blunt incision along which the device may be advanced. In this step, the device is located outward of the tunneler relative to the patient's body. At 520 the handle, carrying the device is rotated so that the device is now inward of the tunneler relative to the patient's body. At 530, the device is advanced by the plunger along the handle and along the then inward facing surface of the tunneler subcutaneously into the patient's body. Finally, at 540, the handle and tunneler are removed.

Exemplary embodiments thus described allow for subcutaneous implantation of devices that are minimally invasive. Note that exemplary embodiments may be used in both human and animal patients.

Exemplary embodiments of the present invention being thus described, it will be obvious that the same may be varied in many ways. Such variations are not to be regarded as a departure from the spirit and scope of the exemplary embodiments of the invention, and all such modifications as would be obvious to one skilled in the art are intended to be included within the scope of the invention.

What is claimed is:

1. A system comprising:
a medical device comprising a first electrode; and
an implantation tool for implanting the medical device in subcutaneous tissue, the tool comprising:
a tool body defining a longitudinal axis and a channel extending along the longitudinal axis, the channel having a distal opening, wherein the tool body is configured to receive the medical device within the channel; and
a plunger slidably fitting within the channel and movable within the channel towards the distal opening, wherein the plunger is configured to push a proximal end of the medical device out of the channel through the distal opening,
wherein a portion of a lateral surface of the tool body defines a lateral opening, separate from the distal opening, to allow visualization of at least a portion of an entire length of the medical device within the channel from a position lateral to the tool body, the entire length of the medical device extending from a proximal end of the medical device to a distal end of the medical device, and wherein the lateral opening allows visualization of at least a portion of the plunger within the channel from a position lateral to the tool body,
wherein the tool body comprises:
a first portion comprising a first proximal end and a first distal end; and
a second portion including the portion of the lateral surface of the tool body that defines the lateral opening, the second portion comprising a second proximal end and a second distal end,
wherein the first proximal end of the first portion adjoins the second distal end of the second portion, and the first portion extends distally from the second distal end of the second portion,
wherein each dimension of a cross section of the first portion at the first proximal end in a first plane orthogonal to the longitudinal axis is less than each corresponding dimension of a cross section of the second portion at the second distal end in a second plane orthogonal to the longitudinal axis,
wherein the second portion defines the channel, and
wherein a top surface of the first portion extends from a bottom surface of the channel as a continuance of the bottom surface along the longitudinal axis.

2. The system of claim 1, wherein the first distal end of the first portion of the tool body is configured for blunt dissection of the subcutaneous tissue.

3. The system of claim 1, further comprising an incision tool comprising:
an incision tool handle;
a blade extending from a distal end of the incision tool handle; and
a pair of incision tool finger grips on the incision tool handle, wherein each incision tool finger grip of the pair of incision tool finger grips is located on an indent in the incision tool handle, and wherein the pair of incision tool finger grips are located closer to a distal end of the incision tool handle than a proximal end of the incision tool handle.

4. The system of claim 3, further comprising a sterile package, wherein the medical device, the implantation tool, and the incision tool are included within the sterile package.

5. The system of claim 1, wherein the plunger comprises:
a distal plunger portion configured to move in the channel; and
a proximal plunger portion, wherein a cross-section of the proximal plunger portion at a distal end of the proximal plunger portion is larger than a cross-section of the distal plunger portion at a proximal end of the distal plunger portion.

6. The system of claim 1, wherein the medical device comprises two electrodes and is configured to monitor an electrocardiogram of the patient via the two electrodes.

7. The system of claim 6, wherein the two electrodes comprise a first electrode adjacent a proximal end of the medical device and a second electrode adjacent a distal end of the medical device.

8. A system comprising:
an insertable cardiac monitor (ICM) comprising two electrodes and configured to monitor an electrocardiogram of a patient via the two electrodes; and
an implantation tool for implanting the ICM in subcutaneous tissue of the patient, wherein the implantation tool comprises:
a tunneler comprising a first proximal end and a first distal end;
an implantation tool handle comprising a second proximal end and a second distal end, wherein the implantation tool handle defines a channel extending along a longitudinal axis of the implantation tool, the channel having a distal opening at the second distal end and a proximal opening at the second proximal end, wherein the implantation tool handle is configured to receive the ICM within the channel; and
a plunger configured to move in the channel through the proximal opening of the channel,
wherein the plunger is configured to push the ICM out of the channel through the distal opening,
wherein the implantation tool handle defines a lower opening, separate from the distal opening, on a portion of a lower surface of the handle,
wherein the ICM can be observed within the channel through the lower opening,
wherein the tunneler extends distally from the implantation tool handle such that the first proximal end adjoins the second distal end,
wherein a longest dimension of a cross section of the tunneler is shorter than a longest dimension of a cross section of the implantation tool handle,
wherein the cross section of the tunneler and the cross section of the implantation tool handle correspond to a plane orthogonal to the longitudinal axis in which the first proximal end of the tunneler adjoins the second distal end of the implantation tool handle, and
wherein a top surface of the tunneler extends from a bottom surface of the channel as a continuance of the bottom surface along the longitudinal axis.

9. The system of claim 8, wherein each dimension of the cross section of the tunneler at the first proximal end is less than each corresponding dimension of the cross section of the implantation tool handle at the second distal end.

10. The system of claim 8, wherein an area of the cross section of the tunneler at the first proximal end is less than an area of the cross section of the implantation tool handle at the second distal end.

11. The system of claim 8, wherein the first proximal end of the tunneler adjoins the second distal end of the implantation tool at a location closer to the lower surface of the implantation tool handle than an upper surface of the implantation tool handle, and wherein the lower surface is opposite the upper surface.

12. The system of claim 8,
wherein the tunneler is configured to be advanced into the subcutaneous tissue of the patient through an opening in the patient's skin and rotated, by rotation of the tool handle, within the subcutaneous tissue to form a pocket in the subcutaneous tissue via blunt dissection, and
wherein the implantation tool handle is configured to receive the ICM in the channel such that the ICM is outward of the tunneler relative to the patient's body as the tunneler is advanced into the subcutaneous tissue and inward of the tunneler relative to the patient's body after rotation of the tool handle.

13. The system of claim 12, wherein the plunger is configured to distally advance along the channel in order to push the ICM out of the channel into the subcutaneous tissue along an inward-facing surface of the tunneler relative to the patient's body, wherein the top surface of the tunneler comprises the inward-facing surface of the tunneler.

14. The system of claim 12, wherein the implantation tool handle includes a first logo which reminds a user of the implantation tool to advance the tunneler into the opening in the patient's skin, wherein the first logo comprises a first number and a first arrow.

15. The system of claim 14, wherein the implantation tool handle includes a second logo which reminds a user of the implantation tool to rotate the handle after advancing the tunneler into the opening in the patient's skin, wherein the logo comprises a second number and a second arrow.

16. The system of claim 8, wherein the lower opening extends along the portion of the lower surface of the implantation tool handle from a first location to a second location, wherein the first location is distal of the proximal end of the implantation tool handle, wherein the second location is proximal of the distal end of the implantation tool handle, and wherein the second location is distal of the first location.

17. The system of claim 16, wherein a distance between the second location and the distal end of the implantation tool handle is greater than a distance between the first location and the proximal end of the implantation tool handle.

18. The system of claim 8, wherein an outer configuration of the ICM comprises an elongated rectangular prism, and wherein the ICM comprises a rounded distal end portion.

19. The system of claim 18, wherein an inner surface of the channel is configured to correspond to the outer configuration of the ICM to prevent rotation of the ICM within the implantation tool handle.

20. The system of claim 19, wherein the inner surface of the channel includes:
one or more corner surfaces, wherein each corner surface of the one or more corner surfaces corresponds to a respective corner of the ICM; and
one or more side surfaces, wherein each side surface of the one or more side surfaces corresponds to a respective side of the ICM.

21. The system of claim 18, wherein the outer configuration of the ICM includes rounded corners.

22. The system of claim 18, wherein the ICM includes a length, a width, and a depth, wherein the width of the ICM is greater than the depth of the ICM such that the ICM has radial asymmetry along a longitudinal axis of the ICM, the radial asymmetry maintaining an orientation of the ICM within the subcutaneous tissue by preventing the ICM from rotating about the longitudinal axis of the ICM.

23. The system of claim 22, wherein an area of a largest cross-section of the ICM is greater than an area of a largest cross-section of the tunneler.

24. The system of claim 22, wherein a length of the tunneler is greater than the length of the ICM.

25. The system of claim 8, wherein the tunneler extends distally from the distal end of the implantation tool handle laterally displaced from the ICM when the ICM is within the channel.

26. The system of claim 8, wherein a distal end of the tunneler is tapered.

27. The system of claim 8, wherein the implantation tool handle comprises one or more implantation tool finger grips, wherein the one or more implantation tool finger grips extend radially from the implantation tool handle such that the one or more implantation tool finger grips are perpendicular to a longitudinal axis of the implantation tool handle.

28. The system of claim 27, wherein the one or more implantation tool finger grips allow a user of the implantation tool to hold the implantation tool handle while placing a finger on a proximal end of the plunger to advance the plunger into the channel.

29. A system comprising:
an insertable cardiac monitor (ICM) comprising a plurality of electrodes and configured to monitor an electrocardiogram of a patient via the electrodes;
an implantation tool for implanting the ICM in subcutaneous tissue of a patient, wherein the implantation tool comprises:
a tunneler comprising a first proximal end and a first distal end;
an implantation tool handle comprising a second proximal end and a second distal end, wherein the implantation tool handle defines a channel extending along a longitudinal axis of the implantation tool, the channel having a distal opening at the second distal end and a proximal opening at the second proximal end, wherein the implantation tool handle is configured to receive the ICM within the channel;
a plunger configured to move in the channel through the proximal opening of the channel, wherein the plunger comprises:
a distal plunger portion configured to move in the channel; and
a proximal plunger portion, wherein a cross-section of the proximal plunger portion at a distal end of the proximal plunger portion is larger than a cross-section of the distal plunger portion at a proximal end of the distal plunger portion,
wherein the plunger is configured to push the ICM out of the channel through the distal opening,
wherein the implantation tool handle defines a lower opening, separate from the distal opening, on a portion of a lower surface of the handle,
wherein the ICM can be observed within the channel through the lower opening,
wherein the tunneler extends distally from the implantation tool handle such that the first proximal end adjoins the second distal end,
wherein a longest dimension of a cross section of the tunneler is shorter than a longest dimension of a cross section of the implantation tool handle, and wherein the cross section of the tunneler and the cross section of the implantation tool handle correspond to a plane orthogonal to the longitudinal axis in which the first proximal end of the tunneler adjoins the second distal end of the implantation tool handle, and wherein a top surface of the tunneler extends from a bottom surface of the channel as a continuance of the bottom surface along the longitudinal axis; and an incision tool comprising:
  an incision tool handle; and
  a blade extending from a distal end of the incision tool handle.

30. A system comprising:

an insertable cardiac monitor (ICM) for monitoring an electrocardiogram of a patient;

an implantation tool for implanting the ICM in subcutaneous tissue of the patient, wherein the implantation tool comprises:
  a tunneler comprising a first proximal end and a first distal end;
  an implantation tool handle comprising a second proximal end and a second distal end, wherein the implantation tool handle defines a channel extending along a longitudinal axis of the implantation tool, the channel having a distal opening at the second distal end and a proximal opening at the second proximal end, wherein the implantation tool handle is configured to receive the ICM within the channel;
  means for moving the ICM through the channel, wherein the means for moving the ICM through the channel comprises:
    a distal portion configured to move in the channel; and
    a proximal portion, wherein a cross-section of the proximal portion at a distal end of the proximal portion is larger than a cross-section of the distal portion at a proximal end of the distal portion,
  wherein the means for moving the ICM through the channel is configured to push the ICM out of the channel through the distal opening,
  wherein the implantation tool handle defines a lower opening, separate from the distal opening, on a portion of a lower surface of the handle,
  wherein the ICM can be observed within the channel through the lower opening,
  wherein the tunneler extends distally from the implantation tool handle such that the first proximal end adjoins the second distal end,
  wherein a longest dimension of a cross section of the tunneler is shorter than a longest dimension of a cross section of the implantation tool handle,
  wherein the cross section of the tunneler and the cross section of the implantation tool handle correspond to a plane orthogonal to the longitudinal axis in which the first proximal end of the tunneler adjoins the second distal end of the implantation tool handle, and
  wherein a top surface of the tunneler extends from a bottom surface of the channel as a continuance of the bottom surface along the longitudinal axis;

an incision tool comprising:
  an incision tool handle; and
  a blade extending from a distal end of the incision tool handle; and a sterile package, wherein the ICM, the implantation tool, and the incision tool are included within the sterile package.

* * * * *